United States Patent
Ho et al.

(10) Patent No.: US 9,265,909 B2
(45) Date of Patent: Feb. 23, 2016

(54) ADJUSTABLE HEADGEAR

(75) Inventors: Peter Chi Fai Ho, Pittsburgh, PA (US);
Elizabeth Powell Margaria, Pittsburgh, PA (US); Justin Rothermel, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 495 days.

(21) Appl. No.: 13/141,201

(22) PCT Filed: Nov. 21, 2009

(86) PCT No.: PCT/IB2009/055264
§ 371 (c)(1),
(2), (4) Date: Jun. 21, 2011

(87) PCT Pub. No.: WO2010/073142
PCT Pub. Date: Jul. 1, 2010

(65) Prior Publication Data
US 2011/0253143 A1 Oct. 20, 2011

Related U.S. Application Data

(60) Provisional application No. 61/140,304, filed on Dec. 23, 2008.

(51) Int. Cl.
*A61M 16/06* (2006.01)
*A62B 18/08* (2006.01)
*A62B 18/02* (2006.01)

(52) U.S. Cl.
CPC ... *A61M 16/0683* (2013.01); *A61M 2210/0618* (2013.01)

(58) Field of Classification Search
CPC . A61M 16/00; A61M 16/06; A61M 16/0683; A61M 16/0497; A61M 1/28; A61M 11/00; A61M 15/0015; A61M 15/0018; A61M 15/0021; A61M 16/0006; A61M 16/0051; A61M 16/0057; A61M 16/0066; A61M 16/0069; A61M 16/0087; A61M 16/04; A61M 16/0488; A61M 16/0493; A61M 16/0605; A61M 16/0611; A61M 16/0616; A61M 16/0622; A61M 16/0633; A61M 16/0638; A61M 16/065; A61M 16/0655; A61M 16/0666; A61M 16/0694; A61M 16/08; A61M 16/0816; A61M 16/0825; A61M 16/0875; A61M 16/10; A61M 16/1065; A61M 16/1075; A61M 16/109; A61M 16/1095; A61M 25/02; A61M 37/00; A41D 13/05; A41D 13/11; A41D 13/1161; A42B 1/24; A42B 3/00; A42B 3/04; A42B 3/288; A44B 11/02; A44B 11/25; A44B 11/2519; A44B 11/2546; A44B 11/2553; A44B 11/266; A61B 18/02; A61B 5/00; A61B 5/01; A61B 5/024; A61B 5/08; A61B 5/097; A61B 5/145; A61B 5/6819; A61B 5/682; A61F 13/00; A61F 5/56; A61H 23/02; A61H 23/0236; A62B 17/00; A62B 17/04; A62B 18/00; A62B 18/02; A62B 18/025; A62B 18/08; A62B 18/084; A62B 18/10; A62B 19/00; A62B 23/02; A62B 23/025; A62B 7/00; A62B 7/10; A62B 9/00; A62B 9/04; A62B 9/06; A63B 71/10; B01D 46/521; B29C 45/0062; B29C 45/1676; B63C 11/02; B63C 11/12; C10L 1/328; F16K 15/14; F16K 15/148

USPC ............ 128/200.24, 202.27, 205.25, 206.21, 128/206.27, 207.11, 207.17, 200.26, 128/201.11, 201.15, 201.18, 201.19, 128/201.22, 201.23, 201.24, 201.25, 128/202.28, 204.17, 204.18, 204.23, 128/204.27, 205.13, 205.23, 205.24, 128/205.27, 205.29, 206.11, 206.12, 128/206.13, 206.14, 206.15, 206.16, 128/206.17, 206.18, 206.19, 206.23, 128/206.24, 206.25, 206.26, 206.28, 128/206.29, 207.12, 207.13, 207.14, 128/207.18, 845, 846, 848, 912, DIG. 26; 2/171.2, 173, 174, 206, 416, 421, 422, 2/424, 425, 428, 452, 5, 6.2, 9; 24/197, 24/198, 200, 3.13, 487, 562, 479.09, 24/DIG. 53

See application file for complete search history.

(56) References Cited

U.S. PATENT DOCUMENTS

| | | | | |
|---|---|---|---|---|
| 4,249,529 | A * | 2/1981 | Nestor et al. | 128/207.17 |
| 4,671,271 | A * | 6/1987 | Bishop et al. | 128/206.11 |
| 5,181,507 | A * | 1/1993 | Michel et al. | 128/201.25 |
| 5,191,882 | A * | 3/1993 | Vogliano | 128/207.11 |
| 5,265,595 | A * | 11/1993 | Rudolph | 128/204.18 |
| 5,429,126 | A * | 7/1995 | Bracken | 128/207.11 |
| 5,429,683 | A * | 7/1995 | Le Mitouard | 128/206.24 |
| 5,517,986 | A | 5/1996 | Starr et al. | |
| 5,522,404 | A * | 6/1996 | Williams | 128/876 |
| 5,533,506 | A * | 7/1996 | Wood | 128/207.18 |
| 5,934,276 | A * | 8/1999 | Fabro et al. | 128/207.17 |
| 6,119,694 | A | 9/2000 | Correa et al. | |
| 6,422,238 | B1 * | 7/2002 | Lithgow | 128/207.11 |
| 6,497,232 | B2 * | 12/2002 | Fecteau et al. | 128/207.11 |
| 6,536,435 | B1 * | 3/2003 | Fecteau et al. | 128/207.11 |

| | | | |
|---|---|---|---|
| 6,776,161 | B2* | 8/2004 | Horn ............... 128/207.11 |
| 6,860,270 | B2* | 3/2005 | Sniadach ............... 128/207.14 |
| 7,069,932 | B2 | 7/2006 | Eaton et al. |
| 7,296,575 | B1 | 11/2007 | Radney |
| 7,509,958 | B2* | 3/2009 | Amarasinghe et al. .. 128/206.24 |
| 7,762,257 | B2* | 7/2010 | Chiam ............... 128/206.21 |
| 2004/0112377 | A1 | 6/2004 | Amarasinghe et al. |
| 2006/0060200 | A1* | 3/2006 | Ho et al. ............... 128/206.24 |
| 2007/0095348 | A1* | 5/2007 | Fisher et al. ............. 128/206.12 |
| 2007/0235033 | A1 | 10/2007 | Reier |
| 2007/0267022 | A1 | 11/2007 | Chiam |
| 2008/0041390 | A1 | 2/2008 | Radney |
| 2008/0230068 | A1 | 9/2008 | Rudolph |
| 2008/0245369 | A1 | 10/2008 | Matula |

FOREIGN PATENT DOCUMENTS

| | | |
|---|---|---|
| CN | 1735439 A | 2/2006 |
| JP | 2006505310 A | 2/2006 |
| JP | 2008541955 A | 11/2008 |
| WO | WO0074758 A1 | 12/2000 |
| WO | WO2005086943 A2 | 9/2005 |
| WO | WO2007133332 A2 | 11/2007 |
| WO | WO2008106716 A1 | 9/2008 |

* cited by examiner

*Primary Examiner* — Annette Dixon

(74) *Attorney, Agent, or Firm* — Michael W. Haas

(57) ABSTRACT

An adjustable headgear assembly (10) for securing a respiratory interface device (26) to the head of a patient that includes a headgear member (12) that fits over the crown and back portion of a human head. The headgear member (12) has upper side portions (14) positionable above and forward of the ears of a human head and lower side portions (16) positionable below the ears and along the back portion of the head. A pair of upper retention members (20) are provided. Each pair of upper retention members (20) extends downwardly and forwardly from the upper side portions (14). A pair of lower retention members (30) extend forwardly and upwardly from each of the side portions. Each pair of upper (20) and lower (30) retention members are structured to engage a respiratory interface device (26).

20 Claims, 9 Drawing Sheets

ADJUSTABLE HEADGEAR

CROSS-REFERENCE TO RELATED APPLICATION

This patent application claims the priority benefit under 35 U.S.C. §119(e) of U.S. Provisional Application No. 61/140,304 filed on Dec. 23, 2008, the contents of which are herein incorporated by reference.

FIELD OF THE INVENTION

The invention relates generally to adjustable headgear assemblies and, more particularly, to adjustable headgear assemblies used in conjunction with respiratory interface devices.

BACKGROUND OF THE INVENTION

Respiratory interface devices are used for various reasons. Typically a respiratory interface device includes a mask portion interconnected with a source of breathable fluid to be inhaled by a patient. Examples of uses of these devices include the delivery of anesthesia, non-invasive ventilation, and for providing positive air pressure to a patient in the treatment of obstructive sleep apnea. In the treatment of obstructive sleep apnea, positive air pressure is provided to a patient while the patient is sleeping.

Accordingly, in uses such as the treatment of obstructive sleep apnea, mask comfort is important to ensure that the patient may sleep and also to ensure that the patient complies with the treatment. For the treatment of obstructive sleep apnea, the mask must provide a sufficient seal to enable pressure to be maintained within the airway of the patient.

Typical respiratory interface devices are bulbous and enclose a large portion of the nose and engage the face of the patient. Additionally, such devices are typically secured to a patient's head via the use of multiple straps and other apparatus. It is common for such devices to include a forehead support and related straps to counteract the forces exerted on the device by the conduit or other member supplying the breathable fluid to the mask and thus maintain proper alignment of the mask. These devices tend to be cumbersome to position and secure on a patient's head and also produce a claustrophobic effect on the patient. Examples of such devices and related headgear can be found in U.S. Pat. Nos. 5,517,986; 6,119,694, and 7,069,932.

SUMMARY OF THE INVENTION

In one embodiment, the invention provides an adjustable headgear assembly comprising a headgear member structured to fit over the crown and back portion of a human head. The headgear member includes upper side portions positionable at least one of above and forward of the ears of a human head and lower side portions positionable at least one of below the ears of a human head and along the back portion of a human head. The headgear assembly further comprises a pair of upper retention members, one of the pair of upper retention members extending downwardly and forwardly from each of the upper side portions and a pair of lower retention members, one of the pair of lower retention members extending forwardly and upwardly from each of the lower side portions. Each of the pair of upper retention members and each of the pair of lower retention members are structured to engage a respiratory interface device.

The pair of upper retention members and the pair of lower retention members may be structured to adjustably retain the respiratory interface device on a human head. Each of the pair of upper retention members may extend downwardly at an angle of between 5 degrees and 40 degrees and each of the pair of lower retention members may extend upwardly at an angle of between 5 degrees and 25 degrees. Each of the pair of upper retention members may comprise a strap member having a hook and loop portion structured to adjustably engage the respiratory interface device and each of the lower retention members may comprise a strap member having a hook and loop portion structured to adjustably engage the respiratory interface device.

The upper retention members and the lower retention members may be integrally formed with the headgear member. Each upper side portion may include a reinforcement member coupled thereto. Each of the upper strap members may be adjustably coupled to a respective one of the upper side portions. Each of the upper retention members may include an elastic portion and each of the lower retention members may include an elastic portion. Each of the upper retention members and each of the lower retention members may be adjustably coupled to the headgear member. One of the upper elastic members may comprise a first portion of a unitary elastic member and a corresponding one of the lower elastic members may comprise a second portion of the unitary elastic member. Each of the upper retention members may include a generally inelastic portion and each of the lower retention members may include a generally inelastic portion. Each of the upper retention members may comprise a first portion of a unitary member and a corresponding one of the lower retention members may comprise a second portion of a unitary member.

Each unitary member may include a first end coupled to one of the upper side portions, an opposite second end adjustably coupled to a corresponding one of the lower side portions, and an intermediate portion disposed between the first end and the opposite second end, with the intermediate portion being structured to engage a respiratory interface device. Each unitary member may include a first end adjustably coupled to one of the upper side portions, an opposite second end coupled to a corresponding one of the lower side portions, and an intermediate portion disposed between the first end and the opposite second end, the intermediate portion being structured to engage a respiratory interface device. Each unitary member may include a first end adjustably coupled to one of the upper side portions, an opposite second end adjustably coupled to a corresponding one of the lower side portions, and an intermediate portion disposed between the first end and the opposite second end, with the intermediate portion being structured to engage a respiratory interface device.

The headgear member may further include a secondary adjustment member having a first end and an opposite second end, the first end being coupled to one of the upper side portions and the second end being adjustably coupled to a corresponding one of the lower side portions. The second end of the secondary adjustment member may be further coupled to the opposite second end of the unitary member. The other one of the upper retention members may comprise a fourth portion of the elastic member and the other one of the lower retention members may comprise a third portion of the unitary member. The unitary member may be adjustably coupled to the headgear member. Each of the lower side portions may include an upward extending portion terminating at an adjustable portion, the adjustable portion engaging a respective one of the upper retention members.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise

DESCRIPTION OF THE PREFERRED EMBODIMENTS

Figure 1:
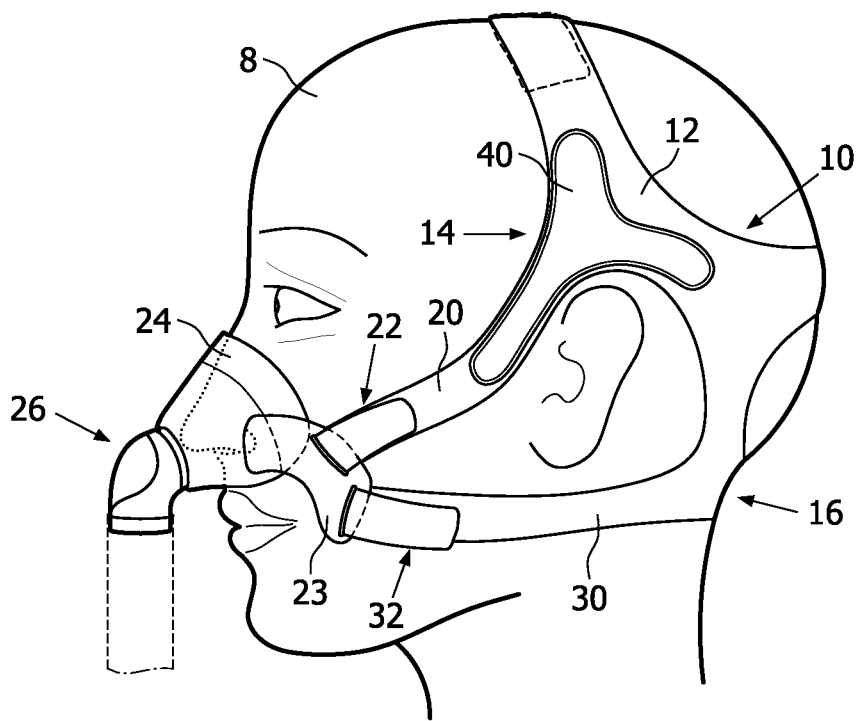
FIG. 1 is a side view of a headgear assembly in accordance with an embodiment of the invention shown positioned on a human head.

Directional phrases used herein, such as, for example and without limitation, top, bottom, left, right, upper, lower, front, back, forward, rearward, above and below and derivatives thereof, relate to the orientation of the elements shown in the drawings and are not limiting upon the claims unless expressly recited therein.

As employed herein, the statement that two or more parts or components are "coupled" together shall mean that the parts are joined or operate together either directly or through one or more intermediate parts or components. As employed herein, the term "number" shall mean one or an integer greater than one (i.e., a plurality).

One potential solution to providing less cumbersome respiratory interface devices has been to try to reduce the amount of mounting points and strap members associated with the headgear used in conjunction with a given respiratory interface device. However, most headgears with only a 2-point mounting fail to provide a stable mounting on the patient due to the lack of upper and lower force vectors acting on the respiratory interface device that is typically present in most 4-point or 3-point headgears.

Figure 9:
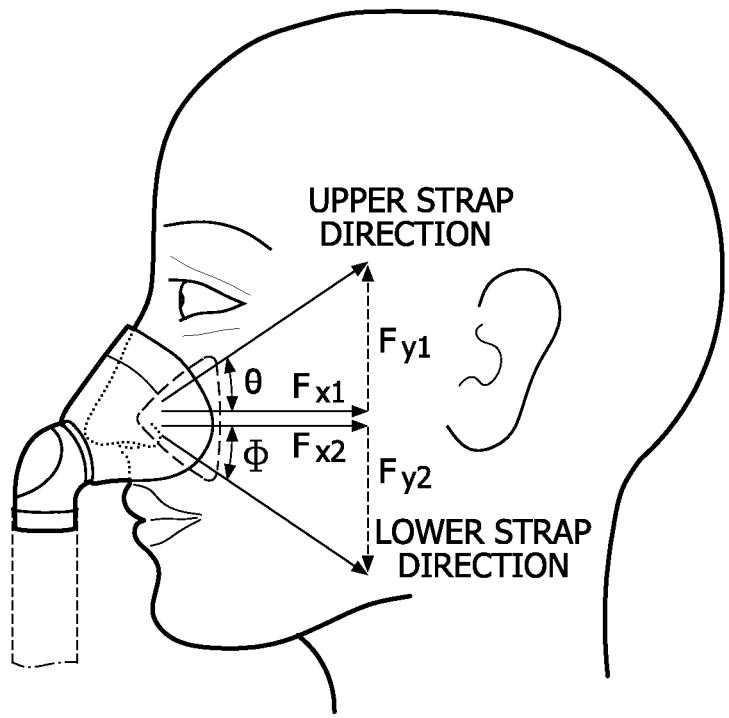
FIG. 9 shows a schematic representation of the forces exerted on a tip of the nose interface device by headgear assemblies in accordance with embodiments of the invention.
Figure 10:
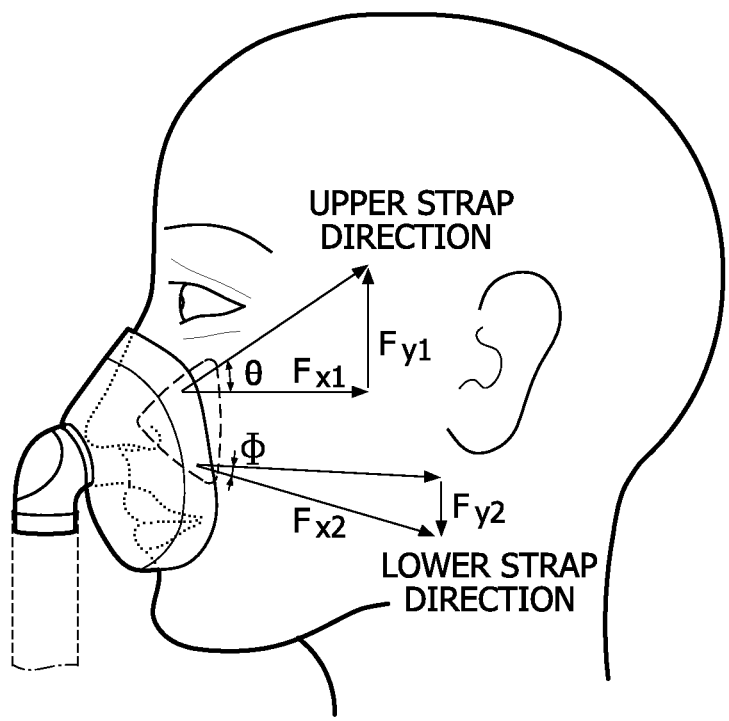
FIG. 10 shows a schematic representation of the forces exerted on a oral-nasal interface device by headgear assemblies in accordance with embodiments of the invention.

The present invention keeps the minimum 2-point mounting attachment with the interface by introducing a dual force strapping connection to achieve maximum stability while minimizing the invasiveness of the respiratory interface device and associated headgear assembly. Accordingly, the invention is directed to a headgear with two (2) mounting points that provides four (4) connecting forces in distinctive upper ($F_{x1}$, $F_{y1}$) and lower ($F_{x2}$, $F_{y2}$) vectors. The result is a headgear with minimum contact providing maximum stability ideally for lower mounting interfaces focusing in the lower half of the face either with tip of the nose coverage or oral-nasal masks. FIGS. 9 and 10, respectively, show examples of the desired forces acting on a tip-of-the-nose device and an oral-nasal mask. The present invention contemplates that, the mounting angle $\theta$ of the upper attachment strap is between five (5) degrees (minimum) and forty (40) degrees (maximum) above the horizontal.

The primary limitation on the placement of the upper straps is the location of the corner of the eyes of a user. Mounting angle $\phi$ of the lower straps is between five (5) degrees (minimum) and twenty to twenty-five (20-25) degrees (maximum) below the horizontal. The minimum lower strap range is generally limited by the location of the ear lobes. Additionally, the maximum lower strap range is limited by the base of the neck, if the strap is too low on the neck this will be uncomfortable for patients, and possibly give the impression that the headgear is slipping down. It is to be appreciated that such angle ranges are given for example purposes only and that mounting angles outside of such ranges may be employed in certain applications. In such applications, it is desirable to attempt to maximize the mounting angle between the upper and lower attachment straps.

FIG. 1 shows a side view of a headgear assembly 10 according to an embodiment of the invention that is structured to adjustably retain a respiratory interface device 26 on a human head 8. Headgear assembly 10 includes a headgear member 12 structured to fit over the crown and back portion of human head 8. Headgear member 12 includes a pair of upper side portions 14 (only one shown in FIG. 1) positioned on either side of head 8 generally above and forward of each ear and a pair of lower side portions 16 positioned generally along a back portion of head 8.

In an exemplary embodiment, upper side portions 14 and lower side portions 16 are integrally formed with, and from the same material as headgear member 12. According to an exemplary embodiment of the present invention, headgear member 12 is made of either stretchable or non stretchable fabric, such as made from weaving, knitting, crocheting, knotting, felting or foam lamination. The present invention contemplates using multiple materials on one headgear such as a non stretchable foam lamination member 12 and stretchable fabric such as elastic band for retention members such as 20 and 30 as will be discussed below. Additionally, such materials may be breathable.

Continuing to refer to FIG. 1, headgear assembly 10 further includes a pair of strap-like upper retention members 20 (only one shown in FIG. 1) and a pair of strap-like lower retention members 30 (only one shown in FIG. 1). Each upper retention member 20 includes a first portion (not numbered) coupled to one of upper side portions 14 and a second portion 22 adjustably coupled to a clip member 23 of mask portion 24 of a respiratory interface device 26, such that each upper retention member 20 extends generally downward and forward from a respective one of upper side portions 14 to mask portion 24. Each lower retention member 30 includes a first portion (not numbered) coupled to one of lower side portions 16 and a second portion 32 adjustably coupled to clip member 23 such that each lower retention member 30 extends generally forward from a respective one of lower side portions 16 to mask portion 24. The present invention contemplates that lower retention members 30 engages clip member 23 at or near the points of engagement of upper retention members 20.

In the embodiment shown in FIG. 1, upper retention members 20 and lower retention members 30 are integrally formed with headgear member 12. Additionally, the adjustable coupling of each upper retention member 20 and each lower retention member 30 to mask portion 24 may be accomplished through the use of a hook and loop fastening mechanism (as shown in FIG. 1) or with other suitable means.

The present contemplates that each upper side portions 14 are stiffened, or reinforced, such as through inclusion of a reinforcement member 40 that is provided to each side of headgear member 12 and substantially overlaps each upper side portion 14. Each reinforcement member 40 may be formed from a rigid or semi-rigid material such as, without limitation, silicone, polyurethane, or foam, which is not limited to fabric. It is to be appreciated that a wide variety of sewing techniques such as stitching and piping can be used to stiffen up the fabric or fabrics to create a frame without the need for inserting other materials.

Figure 2:
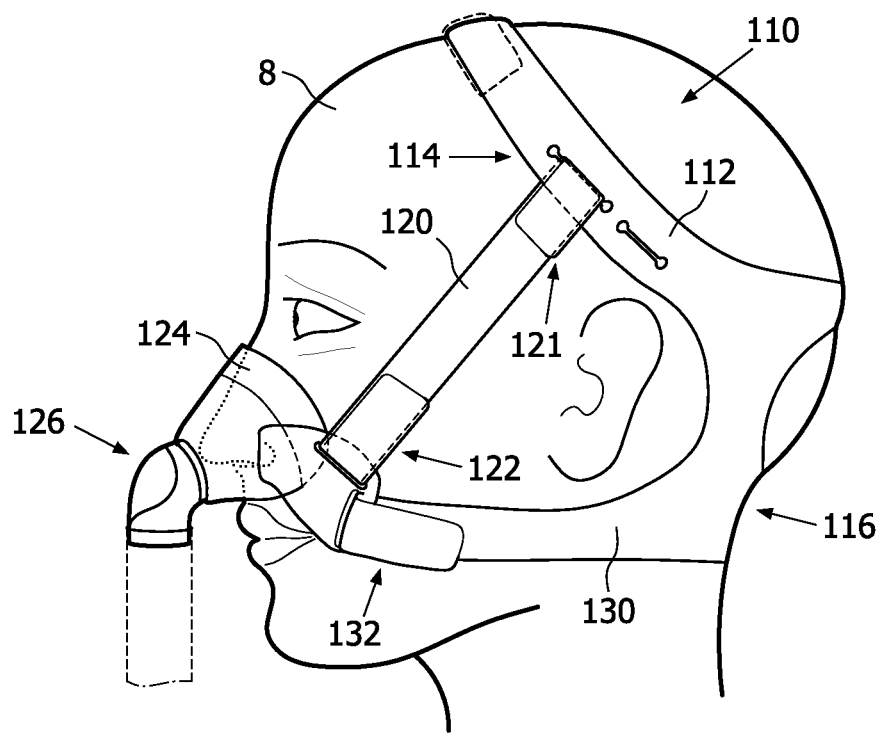
FIGS. 2-8 are side views of headgear assemblies in accordance with other embodiments of the invention shown positioned on a human head.

FIG. 2 shows a side view of a headgear assembly 110 according to an another embodiment of the invention. Headgear assembly 110 includes a headgear member 112 structured to fit over the crown and back portion of human head 8. Headgear member 112 may be made from any fabric such as previously described or similar thereto. However, due to the structural nature of the member, headgear member 112 may be made from a stiff, non-stretchable fabric. Headgear member 112 includes a pair of upper side portions 114 (only one shown in FIG. 2) positioned on either side of head 8 generally above each ear and a pair of lower side portions 116 positioned generally along a back portion of head 8. In an exemplary embodiment, upper side portions 114 and lower side portions 116 are integrally formed with, and from the same material as headgear member 112.

Continuing to refer to FIG. 2, headgear assembly 110 further includes a pair of strap-like upper retention members 120 (only one shown in FIG. 2) and a pair of strap-like lower retention members 130 (only one shown in FIG. 2). Each upper retention member 120 includes a first portion 121 adjustably coupled to one of upper side portions 114 and a second portion 122 adjustably coupled to a mask portion 124 of a respiratory interface device 126 such that each upper retention member 120 extends generally downward and forward from a respective one of upper side portions 114 to mask portion 124. Each lower retention member 130 includes a first portion (not numbered) coupled to one of lower side portions 116 and a second portion 132 adjustably coupled to mask portion 124 such that each lower retention member 130 extends generally forward from a respective one of lower side portions 116 to mask portion 124. The present invention contemplates that lower retention members 130 engages mask portion 124 at or near the points of engagement of upper retention members 120.

In the embodiment shown in FIG. 2, lower retention members 130 are integrally formed with headgear member 112. Additionally, the adjustable couplings of each upper retention member 120 and each lower retention member 130 may be accomplished through the use of a hook and loop fastening mechanism (as shown in FIG. 2) or with other suitable means.

Figure 3:
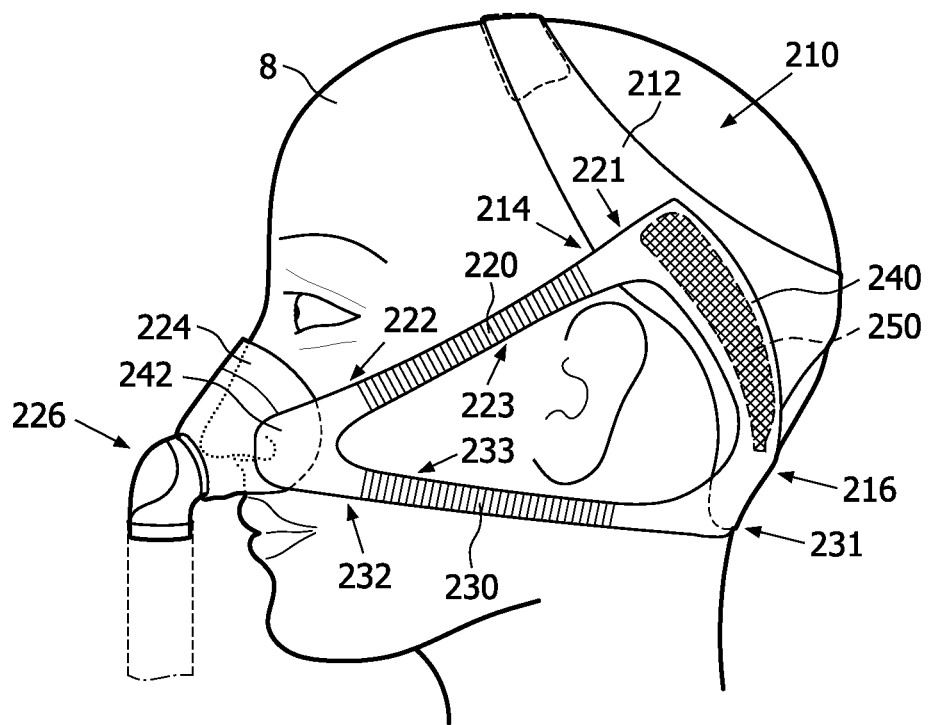

FIG. 3 shows a side view of a headgear assembly 210 according to another embodiment of the invention. Headgear assembly 210 includes a headgear member 212 structured to fit over the crown and back portion of human head 8. The present invention contemplates that headgear member 212 is made of either stretchable or non stretchable fabric, such as made from weaving, knitting, crocheting, knotting, felting or foam lamination. It is common to use multiple materials on one headgear such as elastic band for retention members 220 and 230 as will be discussed below. Additionally, such materials may be breathable. Headgear member 212 includes a pair of upper side portions 214 (only one shown in FIG. 3) positioned on either side of head 8, generally above each ear, and a pair of lower side portions 216 positioned generally along a back portion of head 8.

Continuing to refer to FIG. 3, headgear assembly 210 further includes a pair of upper retention members 220 (only one shown in FIG. 3) and a pair of lower retention members 230 (only one shown in FIG. 3). Each upper retention member 220 includes a first portion 221 adjustably coupled to one of upper side portions 214 and an opposite second portion 222 coupled to a mask portion 224 of respiratory interface device 226 such that each upper retention member 220 extends generally downward and forward from a respective one of upper side portions 214 to mask portion 224. Each lower retention member 230 includes a first portion 231 adjustably coupled to one of lower side portions 216 and a second portion 232 coupled to mask portion 224 such that each lower retention member 230 extends generally forward and upward from a respective one of lower side portions 216 to mask portion 224. Such adjustable couplings may be accomplished through the use of a hook and loop fastening mechanism 250 as shown generally in hidden line in FIG. 3 or with other suitable means.

Each upper retention member 220 further includes an intermediate portion 223 that, in an exemplary embodiment, includes an elastic portion (e.g., without limitation, elastic straps). Similarly, each lower retention member 230 further includes an intermediate portion 233 that, in an exemplary embodiment, includes an elastic portion (e.g., without limitation, elastic strap). The present invention contemplates that such elastic portion may be formed of spandex polyester with an elongation in the range of 150-200%.

As further shown in the embodiment of FIG. 3, first portions 221, 231 of upper and lower retention members 220 and 230 are coupled together by transverse member 240. Additionally, second portions 222, 232 are coupled together by mask engaging member 242 such that second portions 222, 232 generally engage mask portion 224 at a common location.

Figure 4:
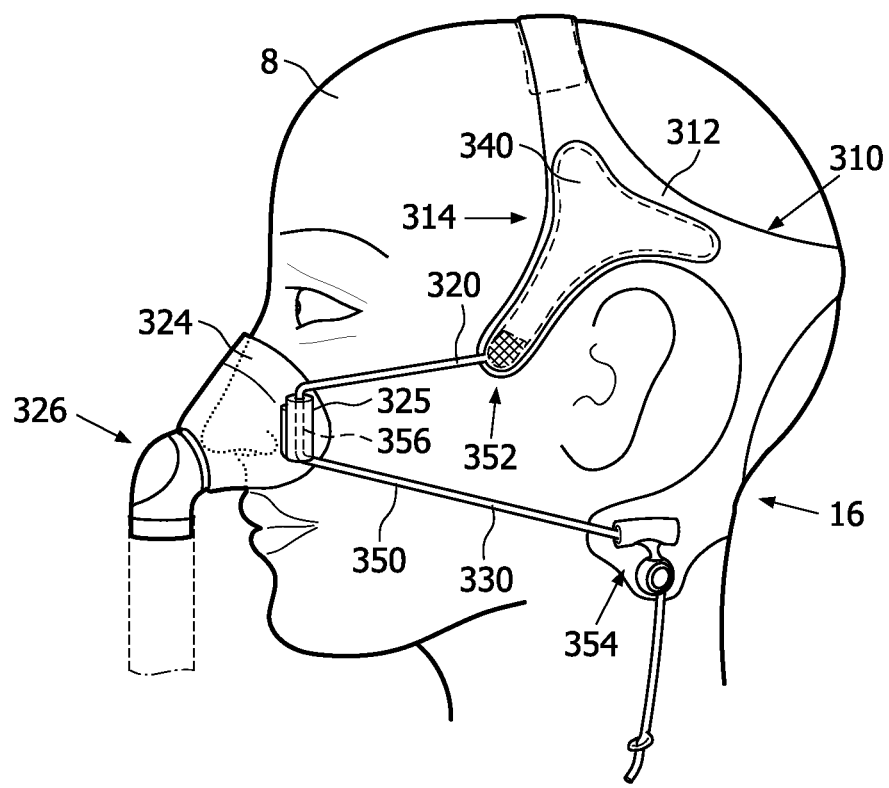

FIG. 4 shows a side view of a headgear assembly 310 according to an other embodiment of the invention that is structured to adjustably retain a respiratory interface device 326 on a human head 8. Headgear assembly 310 includes a headgear member 312 structured to fit over the crown and back portion of human head 8. Headgear member 312 includes a pair of upper side portions 314 (only one shown in FIG. 4) positioned on either side of head 8, generally above and forward of each ear, and a pair of lower side portions 316 positioned generally below and rearward from each ear along a back portion of head 8. In an exemplary embodiment, upper side portions 314 and lower side portions 316 are integrally formed with, and from the same material as headgear member 312. The present invention contemplates that headgear member 312 is made of either stretchable or non stretchable fabric, such as made from weaving, knitting, crocheting, knotting, felting or foam lamination. Additionally, such materials are may be breathable.

Continuing to refer to FIG. 4, headgear assembly 310 further includes a pair of upper retention members 320 (only one shown in FIG. 4) and a pair of lower retention members 330 (only one shown in FIG. 4). In the embodiment of FIG. 4, upper retention member 320 and lower retention member 330 shown are separate portions of a unitary member 350 that, in an exemplary embodiment, is a cord-like member (e.g., without limitation, bungee cord, nylon cord). Unitary member 350 includes a first end portion 352 coupled to one of upper side portions 314, an opposite second end portion 354 adjustably coupled to a corresponding one of the lower side portions 316, and an intermediate portion 356 disposed between first end portion 352 and opposite second end portion 354. Intermediate portion 356 is structured to slidably engage a portion 325 of mask portion 324. As shown in FIG. 4, each upper retention member 320 extends generally downward and forward from a respective one of upper side portions 314 toward mask portion 324. As further shown in FIG. 4, each lower retention member 330 extends generally forward and upward from a respective one of lower side portions 316 to mask portion 324.

In order to provide stiffness to upper side portions 314, a reinforcement member 340 is provided to each side of headgear member 312 substantially overlapping each upper side portion 314. Each reinforcement member 340 is, in an exemplary embodiment, formed from a rigid or semi-rigid material such as, without limitation, silicone, polyurethane, or foam. It is to be appreciated that a wide variety of sewing techniques such as stitching and piping can be used to stiffen the fabric or fabrics to create a frame. Such techniques may be employed in conjunction with, or in lieu of, the reinforcement members 340.

Figure 5:
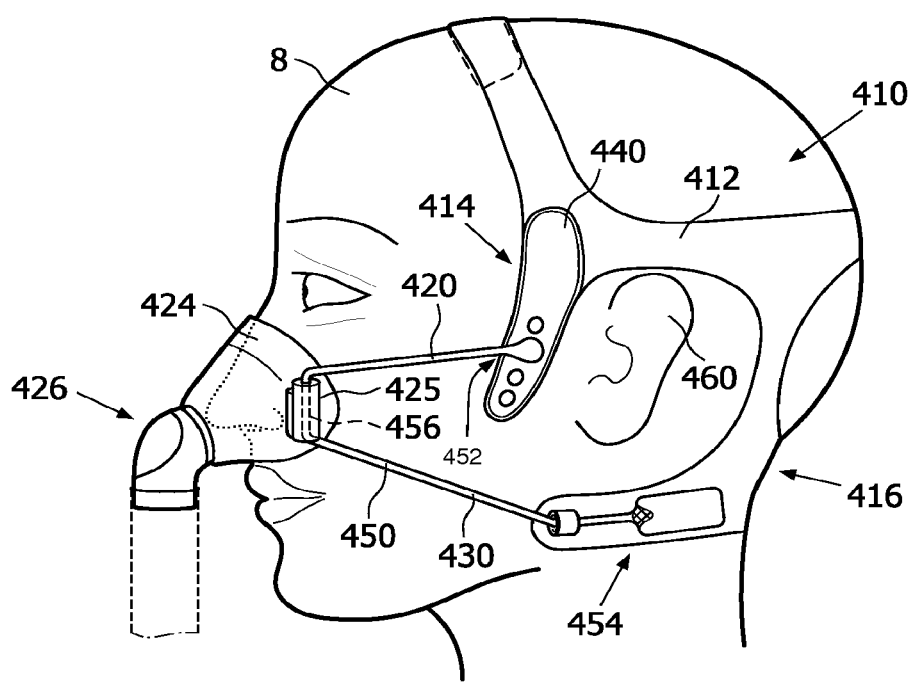

FIG. 5 shows a side view of a headgear assembly 410 according to another embodiment of the invention that is structured to adjustably retain a respiratory interface device 426 on a human head 8. Headgear assembly 410 includes a headgear member 412 structured to fit over the crown and back portion of human head 8. Headgear member 412 includes a pair of upper side portions 414 (only one shown in FIG. 5) positioned on either side of head 8 generally above and forward of each ear and a pair of lower side portions 416 positioned generally below and rearward from each ear along a back portion of head 8. In an exemplary embodiment, upper side portions 414 and lower side portions 416 are integrally formed with, and from the same material as headgear member 412. Headgear member 412 is, in an exemplary embodiment, made of either stretchable or non stretchable fabric, such as made from weaving, knitting, crocheting, knotting, felting or foam lamination. Such materials may be made breathable.

Continuing to refer to FIG. 5, headgear assembly 410 further includes a pair of upper retention members 420 (only one shown in FIG. 5) and a pair of lower retention members 430 (only one shown in FIG. 5). In the embodiment of FIG. 5, the upper retention member 420 and the lower retention member 430 shown are separate portions of a unitary member 450 that is, in an exemplary embodiment, a cord-like member (e.g., without limitation, bungee cord, nylon cord). Unitary member 450 includes a first end portion 452 coupled to one of upper side portions 414 at one of a number of locations 460 that provide for adjustment of the placement of the upper retention member 420 with respect to a user's eye.

Unitary member 450 further includes an opposite second end portion 454 adjustably coupled to a corresponding one of lower side portions 416 and an intermediate portion 456 disposed between first end portion 452 and opposite second end portion 454. Intermediate portion 456 being structured to slidably engage a portion 425 of mask portion 424. As shown in FIG. 5, each upper retention member 420 extends generally downward and forward from a respective one of upper side portions 414 toward mask portion 424. As further shown in FIG. 5, each lower retention member 430 extends generally forward and upward from a respective one of lower side portions 416 to mask portion 424.

In order to provide stiffness to upper side portions 414, a reinforcement member 440 is provided to each side of headgear member 412 substantially overlapping each upper side portion 414. Each reinforcement member 440 is, in an exemplary embodiment, made from a semi rigid polymer such as, without limitation EVA copolymer, polyethylene, polypropylene, polyurethane, vinyl, that is formed through injection molding or die cutting.

Figure 6:
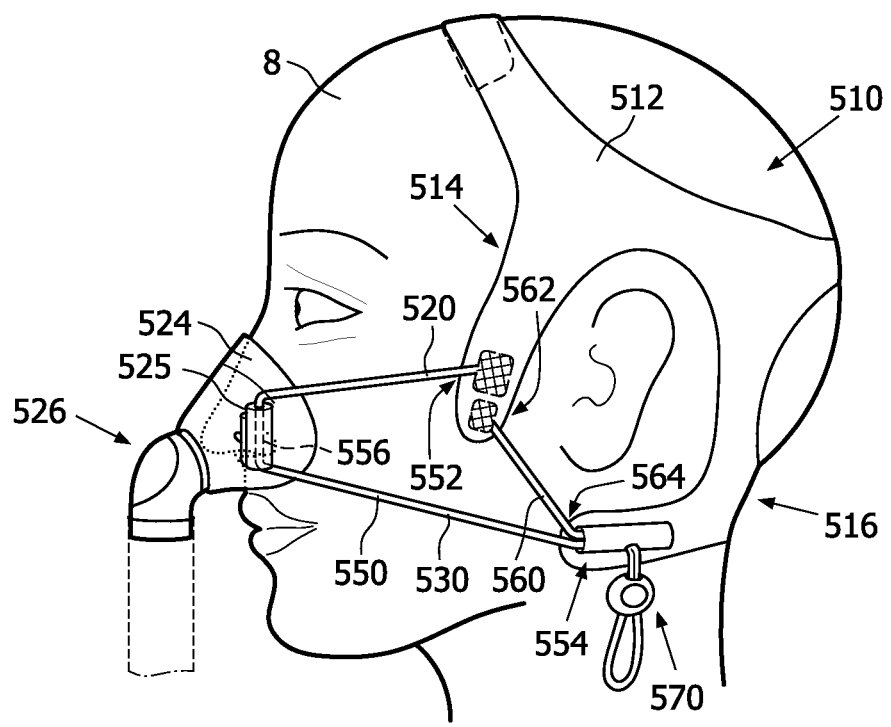

FIG. 6 shows a side view of a headgear assembly 510 according to an embodiment of the invention that is structured to adjustably retain a respiratory interface device 526 on a human head 8. Headgear assembly 510 includes a headgear member 512 structured to fit over the crown and back portion of human head 8. Headgear member 512 includes a pair of upper side portions 514 (only one shown in FIG. 6) positioned on either side of head 8 generally above and forward of each ear and a pair of lower side portions 516 positioned generally below and rearward from each ear along a back portion of head 8. In an exemplary embodiment, upper side portions 514 and lower side portions 516 are integrally formed with, and from the same material as headgear member 512. Headgear member 512 is, in an exemplary embodiment, made of either stretchable or non stretchable fabric, such as made from weaving, knitting, crocheting, knotting, felting, or foam lamination. Such materials may be breathable.

Continuing to refer to FIG. 6, headgear assembly 510 further includes a pair of upper retention members 520 (only one shown in FIG. 6) and a pair of lower retention members 530 (only one shown in FIG. 6). In the embodiment of FIG. 6, upper retention member 520 and lower retention member 530 shown are separate portions of a unitary member 550 that is, in an exemplary embodiment, a cord-like member (e.g., without limitation, bungee cord, nylon cord). Unitary member 550 includes a first end portion 552 coupled to one of upper side portions 514, an opposite second end portion 554 adjustably coupled to a corresponding one of lower side portions 516, and an intermediate portion 556 disposed between first end portion 552 and opposite second end portion 554. Intermediate portion 556 being structured to slidably engage a portion 525 of mask portion 524. As shown in FIG. 6, each upper retention member 520 extends generally downward and forward from a respective one of upper side portions 514 toward mask portion 524. As further shown in FIG. 6, each lower retention member 530 extends generally forward and upward from a respective one of lower side portions 516 to mask portion 524.

Headgear member 512 further includes a pair of secondary adjustment members 560 (only one shown in FIG. 6). Each of secondary adjustment members 560 having a first end 562 coupled to one of upper side portions 514 and an opposite second end 564 adjustably coupled to a corresponding one of lower side portions 516. In an embodiment, the opposite second end of each of secondary adjustment members 560 is further coupled to opposite second end 554 of unitary member 550. It can be readily appreciated that such arrangement allows for rapid adjustment of headgear assembly 510 by tightening or loosening at two locations 570 (only one location shown in FIG. 6).

Figure 7:
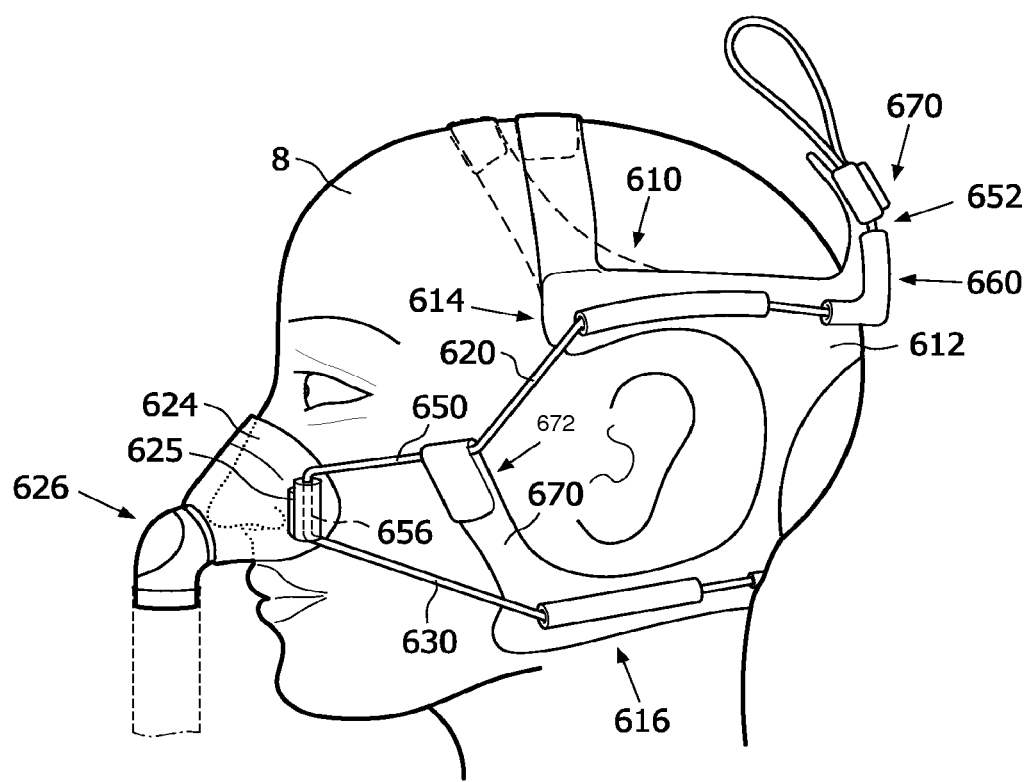

FIG. 7 shows a side view of a headgear assembly 610 according to another embodiment of the invention that is structured to adjustably retain a respiratory interface device 626 on a human head 8. Headgear assembly 610 includes a headgear member 612 structured to fit over the crown and back portion of human head 8. Headgear member 612 includes a pair of upper side portions 614 (only one shown in FIG. 7) positioned on either side of head 8 generally above each ear and a pair of lower side portions 616 positioned generally below each ear. In an exemplary embodiment, upper side portions 614 and lower side portions 616 are integrally formed with, and from the same material as headgear member 612. Headgear member 612 is, in an exemplary embodiment, made of either stretchable or non stretchable fabric, such as made from weaving, knitting, crocheting, knotting, felting or foam lamination. Such materials may be breathable.

Continuing to refer to FIG. 7, headgear assembly 610 further includes a pair of upper retention members 620 (only one shown in FIG. 7), each depending from upper side portions 614, and a pair of lower retention members 630 (only one shown in FIG. 7) each generally extending forward and upward from lower side portions 616. Each lower side portion 616, in an exemplary embodiment, further includes an upward extending portion 670 that terminates at an adjustable portion 672 that engages a respective one of upper retention members 620 and may generally deflect upper retention member 620 away from the eye (not numbered) of a user. Such adjustable portion may include a hook and loop or other suitable fastener.

In the embodiment of FIG. 7, each one of the pair of upper retention members 620 and each one of the pair of lower retention members 630 are separate portions of a unitary member 650. Unitary member 650 is, in an exemplary embodiment, a cord-like member (e.g., without limitation, bungee cord, nylon cord). Unitary member 650 is shown as a continuous loop having a portion 652 that is adjustably coupled to an upper rear portion 660 of headgear member 612. Unitary member 650 may also be formed from a member having two ends (not shown), with the two ends being adjustable coupled to the upper rear portion 660. Unitary member 650 slidably engages headgear member 612 at each of upper side portions 614 as well as at each of lower side portions 616. Additionally, a portion 656 of unitary member 650 slidably engages a portion 625 of mask portion 624.

It is to be appreciated that such arrangement allows for rapid adjustment of headgear assembly 610 by tightening or loosening unitary member 650 at one location 670. Although FIG. 7 shows unitary member 650 adjustably coupled to upper rear portion 660, it can be readily appreciated that such adjustable coupling to headgear member 612 could be made substantially anywhere and still provide similar benefits.

Figure 8:
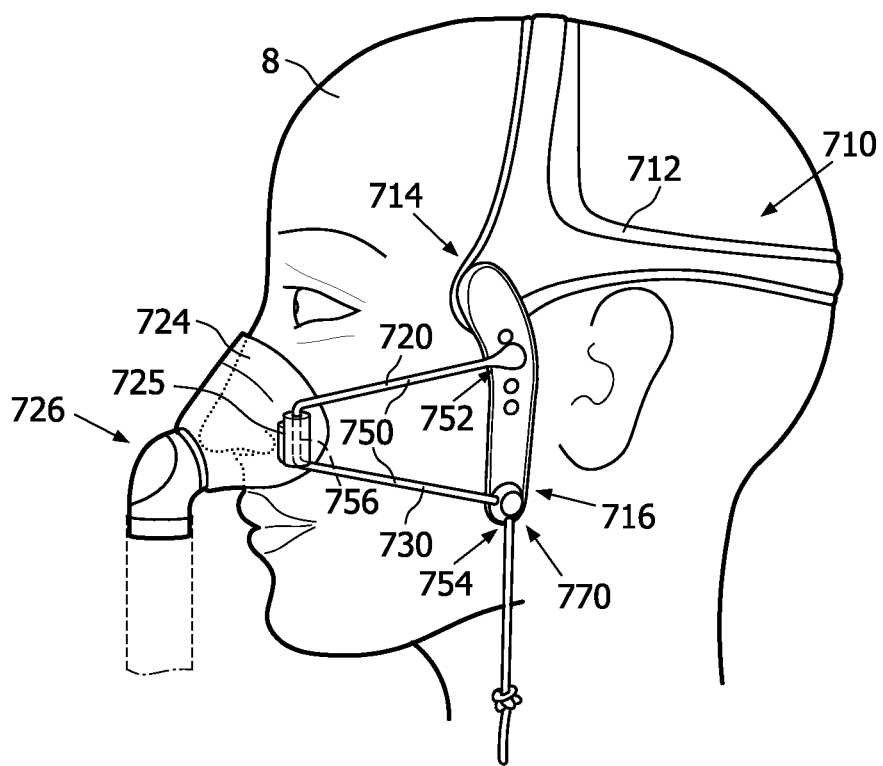

FIG. 8 shows a side view of a headgear assembly 710 according to another embodiment of the invention that is structured to adjustably retain a respiratory interface device 726 on a human head 8. Headgear assembly 710 includes a headgear member 712 structured to fit over the crown and back portion of human head 8. Headgear member 712 includes a pair of upper side portions 714 (only one shown in FIG. 8) positioned on either side of head 8 generally forward and above each ear and a pair of lower side portions 716 (only one shown in FIG. 8) positioned generally below each ear. In an exemplary embodiment, upper side portions 714 and lower side portions 716 are integrally formed with, and from the same material as headgear member 712. Headgear member 712, in an exemplary embodiment, is made of either stretchable or non stretchable fabric, such as made from weaving, knitting, crocheting, knotting, felting or foam lamination. Such materials may be breathable.

Continuing to refer to FIG. 8, headgear assembly 710 further includes a pair of upper retention members 720 (only one shown in FIG. 8) and a pair of lower retention members 730 (only one shown in FIG. 8). In the embodiment of FIG. 8, upper retention member 720 and lower retention member 730 shown are separate portions of a unitary member 750 that are, in an exemplary embodiment, made from a cord-like member (e.g., without limitation, bungee cord, nylon cord). Unitary member 750 includes a first end portion 752 adjustably coupled to one of the upper side portions 714, an opposite second end portion 754 adjustably coupled to a corresponding one of lower side portions 716, and an intermediate portion 756 disposed between first end portion 752 and opposite second end portion 754. Intermediate portion 756 being structured to slidably engage a portion 725 of mask portion 724. As shown in FIG. 8, each upper retention member 720 extends generally downward and forward from a respective one of upper side portions 714 toward to portion 725. As further shown in FIG. 8, each lower retention member 730 extends generally forward and upward from a respective one of lower side portions 716 to portion 725.

It can be readily appreciated that such arrangement allows for rapid adjustment of headgear assembly 710 by tightening or loosening at two locations 770 (only one location shown in FIG. 8).

While exemplary embodiments of the invention have been described and illustrated herein in conjunction with tip-of-the-nose respiratory interface devices, it is to be readily appreciated that the concepts disclosed herein may readily be applied to oral-nasal masks as well as to other mask assemblies.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An adjustable headgear assembly comprising:
   a headgear member structured to fit over the crown and back portion of a human head, said headgear member having upper side portions positionable at least one of above and forward of the ears of a human head and lower side portions positionable at least one of below the ears of a human head and along the back portion of a human head;
   a pair of upper retention members, one of said pair of upper retention members extending downwardly and forwardly from each of said upper side portions; and
   a pair of lower retention members, one of said pair of lower retention members extending forwardly and upwardly from each of said lower side portions, wherein:
      each upper retention member of said pair of upper retention members is positioned and structured to engage a respiratory interface device in a manner which imparts an upward connecting force on the respiratory interface device in an upward direction, wherein each lower retention member of said pair of lower retention members is positioned and structured to engage the respiratory interface device in a manner which imparts a downward connecting force on the respiratory interface device in a downward direction distinct from the upward direction,
      one of the upper retention members comprises a first portion of a first cord-like unitary member and a corresponding one of the lower retention members comprises a second portion of the first cord-like unitary member,
      the other of the upper retention members comprises a first portion of a second cord-like unitary member, and a corresponding one of the lower retention members comprises a second portion of the second cord-like unitary member, and
      each unitary member includes (a) a first end coupled to one of the upper side portions, (b) an opposite second end coupled to a corresponding one of the lower side portions, and (c) an intermediate portion disposed between the first end and the opposite second end, said intermediate portion being structured to slidably engage a vertically extending portion of a respiratory interface device along a vertical axis of the vertically extending portion.

2. The headgear assembly of claim 1, wherein each upper side portion includes a reinforcement member coupled thereto.

3. The headgear assembly of claim 1, wherein each of the upper retention members and each of the lower retention members are adjustably coupled to the headgear member.

4. The headgear assembly of claim 1, wherein said headgear member further includes a secondary adjustment member having a first end and an opposite second end, said first end being coupled to one of the upper side portions and said second end being adjustably coupled to a corresponding one of the lower side portions.

5. The headgear assembly of claim 4, wherein the second end of said secondary adjustment member is further coupled to the opposite second end of said unitary member.

6. The headgear assembly of claim 1, wherein the first cord-like unitary member and the second cord-like unitary member comprise portions of a single unitary member.

7. The headgear assembly of claim 6, wherein said single unitary member is adjustably coupled to said headgear member.

8. The headgear assembly of claim 7, wherein each of the lower side portions include an upward extending portion that terminates at an adjustable portion, the adjustable portion engaging a respective one of the upper retention members.

9. The headgear assembly of claim 1, wherein each cord-like unitary member is an elastic member.

10. The headgear assembly of claim 1, wherein each upper retention member extends downwardly at an angle of between 5 degrees and 40 degrees and each lower retention member extends upwardly at an angle of between 5 degrees and 25 degrees.

11. A patient interface assembly comprising:
  (a) a respiratory interface device structured to sealingly engage about one or more of the nose and mouth of a patient, the respiratory interface device comprising a vertically extending portion; and
  (b) a headgear assembly comprising:
    (1) a headgear member structured to fit over the crown and back portion of a human head, said headgear member having upper side portions positionable at least one of above and forward of the ears of a human head and lower side portions positionable at least one of below the ears of a human head and along the back portion of a human head;
    (2) a pair of upper retention members, one of said pair of upper retention members extending downwardly and forwardly from each of said upper side portions; and
    (3) a pair of lower retention members, one of said pair of lower retention members extending forwardly and upwardly from each of said lower side portions,
  wherein each upper retention member of said pair of upper retention members engages the respiratory interface device in a manner which imparts an first connecting force on the respiratory interface device directed in an upward direction,
  wherein each lower retention member of said pair of lower retention members engages the respiratory interface device in a manner which imparts a second connecting force on the respiratory interface device directed in a downward direction,
  wherein one of the upper retention members comprises a first portion of a first cord-like unitary member and a corresponding one of the lower retention members comprises a second portion of the first cord-like unitary member,
  wherein the other of the upper retention members comprises a first portion of a second cord-like unitary member, and a corresponding one of the lower retention members comprises a second portion of the second cord-like unitary member
  wherein each unitary member includes:
    (i) a first end coupled to one of the upper side portions;
    (ii) an opposite second end coupled to a corresponding one of the lower side portions; and
    (iii) an intermediate portion disposed between the first end and the opposite second end, said intermediate portion slidably engaging the vertically extending portion of a respiratory interface device along a vertical axis of the vertically extending portion.

12. The patient interface assembly of claim 11, wherein each upper retention member extends downwardly at an angle of between 5 degrees and 40 degrees and each lower retention member extends upwardly at an angle of between 5 degrees and 25 degrees.

13. The patient interface assembly of claim 11, wherein each upper side portion includes a reinforcement member coupled thereto.

14. The patient interface assembly of claim 11, wherein each of the upper retention members and each of the lower retention members are adjustably coupled to the headgear member.

15. The patient interface assembly of claim 11, wherein said headgear member further includes a secondary adjustment member having a first end and an opposite second end, said first end being coupled to one of the upper side portions and said second end being adjustably coupled to a corresponding one of the lower side portions.

16. The patient interface assembly of claim 15, wherein the second end of said secondary adjustment member is further coupled to the opposite second end of said unitary member.

17. The patient interface assembly of claim 11, wherein the first cord-like unitary member and the second cord-like unitary member comprise portions of a single unitary member.

18. The patient interface assembly of claim 17, wherein said single unitary member is adjustably coupled to said headgear member.

19. The patient interface assembly of claim 18, wherein each of the lower side portions include an upward extending portion that terminates at an adjustable portion, the adjustable portion engaging a respective one of the upper retention members.

20. The patient interface assembly of claim 11, wherein each cord-like unitary member is an elastic member.

* * * * *